United States Patent
Clemens et al.

(10) Patent No.: US 6,510,348 B2
(45) Date of Patent: Jan. 21, 2003

(54) PERFUSION LEAD AND METHOD OF USE

(75) Inventors: William W. Clemens, Fridley, MN (US); Douglas N. Hess, Maple Grove, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/745,107

(22) Filed: Dec. 20, 2000

(65) Prior Publication Data
US 2002/0077684 A1 Jun. 20, 2002

(51) Int. Cl.⁷ .............................................. A61N 1/05
(52) U.S. Cl. ...................................................... 607/119
(58) Field of Search ................................. 607/119, 120, 607/122, 116

(56) References Cited

U.S. PATENT DOCUMENTS

| | | | |
|---|---|---|---|
| 4,161,952 A | 7/1979 | Kinney et al. | 128/786 |
| 4,350,169 A | 9/1982 | Dutcher et al. | 128/783 |
| 4,355,646 A | 10/1982 | Kallok et al. | 128/786 |
| 4,381,013 A | 4/1983 | Dutcher | 128/785 |
| 4,506,680 A | 3/1985 | Stokes | 128/786 |
| 4,545,390 A | 10/1985 | Leary | 128/772 |
| 4,559,951 A * | 12/1985 | Dahl et al. | |
| 4,577,642 A | 3/1986 | Stokes | 128/784 |
| 4,606,118 A | 8/1986 | Cannon et al. | 29/825 |
| 4,711,251 A | 12/1987 | Stokes | 128/784 |
| 4,815,478 A | 3/1989 | Buchbinder et al. | 128/772 |
| 4,903,701 A | 2/1990 | Moore et al. | 128/419 PG |
| 4,922,926 A | 5/1990 | Hirschberg et al. | |
| 4,967,755 A | 11/1990 | Pohndorf | 128/675 |
| 5,016,646 A | 5/1991 | Gotthardt et al. | 128/784 |
| 5,081,988 A | 1/1992 | Cook et al. | 128/419 PG |
| 5,087,244 A | 2/1992 | Wolinsky et al. | 604/53 |
| 5,095,915 A | 3/1992 | Engelson | 128/772 |
| 5,246,014 A | 9/1993 | Williams et al. | 607/122 |

(List continued on next page.)

FOREIGN PATENT DOCUMENTS

| | | |
|---|---|---|
| EP | 0 993 841 A1 | 4/2000 |
| WO | WO 99/64104 | 12/1999 |

*Primary Examiner*—Scott M. Getzow
(74) *Attorney, Agent, or Firm*—Girma Wolde-Michael; Michael C. Soldner (57) ABSTRACT

A medical electrical lead including an inflatable member at a distal tip section, and a system of use, are disclosed. The inflation member is adapted to engage the walls of a cardiac vein or coronary artery to occlude the vessel. According to one aspect of the invention, the inflation member is formed of a bio-absorbable material. In another embodiment, the inflation member is a micro-porous material. The lead of the current invention may include a port located distal to the inflation member to deliver radiopaque dye or any other substance to a vessel when the inflation member is in the inflated state. This allows a fluoroscopic image of a patient's vascular system to be obtained while the lead is in place within a vessel. A perfusion lumen may be provided to allow a partial flow of blood to continue around the inflation member when the inflation member is occluding a vessel. In one embodiment, lead is provided with a lumen for receiving a stiffening member such as a stylet to aid in lead placement. According to one method of using the current invention, inflation member may be inflated after the lead is placed at a desired implant site to provide a temporary fixation mechanism during withdrawal of the stiffening member and/or a guide catheter or sheath used to place the lead at the implant site. This temporary fixation mechanism may also be employed to retain a desired lead location while thresholds are obtains. The inflation member may be retained in an inflated state for a longer predetermined period of time until tissue in-growth begins to occur around the lead.

16 Claims, 5 Drawing Sheets

U.S. PATENT DOCUMENTS

| | | | |
|---|---|---|---|
| 5,387,233 A | 2/1995 | Alferness et al. | 607/126 |
| 5,545,149 A | 8/1996 | Brin et al. | 604/265 |
| 5,571,159 A | 11/1996 | Alt | |
| 5,584,873 A | 12/1996 | Shoberg et al. | 607/122 |
| 5,746,710 A | 5/1998 | Nielsen et al. | 609/14 |
| 5,755,704 A | 5/1998 | Lunn | 604/282 |
| 5,811,043 A | 9/1998 | Horrigan et al. | 264/138 |
| 5,845,396 A | 12/1998 | Altman et al. | 29/885 |
| 5,851,226 A | 12/1998 | Skubitz et al. | 607/126 |
| 5,873,842 A | 2/1999 | Brennen et al. | 600/585 |
| 5,935,159 A | 8/1999 | Cross, Jr. et al. | 607/116 |
| 5,957,970 A | 9/1999 | Shoberg et al. | 607/722 |
| 5,964,795 A | 10/1999 | McVenes et al. | 607/122 |
| 5,968,087 A | 10/1999 | Hess et al. | 607/127 |
| 6,006,122 A | 12/1999 | Smits | 600/373 |
| 6,006,137 A | 12/1999 | Williams | 607/119 |
| 6,122,522 A | 9/2000 | Lee | 455/458 |
| 6,136,021 A | 10/2000 | Tockman et al. | |

\* cited by examiner

PERFUSION LEAD AND METHOD OF USE

The following application includes material that is common to U.S. Patent application Ser. No. 09/833,158 filed on even date herewith entitled "Medical Electrical Lead and Method of Use", which is incorporated herein by reference in its entirety.

FIELD OF THE INVENTION

The present invention relates generally to an implantable medical electrical lead; and more particularly, relates to a lead having an occlusion balloon at the distal end of the lead that may be used for obtaining a fluoroscopic image of the vascular system while a lead is located in a vessel, and for temporarily anchoring the lead at a desired implant site.

BACKGROUND OF THE INVENTION

Implantable medical electrical stimulation and/or sensing leads are well known in the fields of cardiac stimulation and monitoring, including cardiac pacing and cardioversion/defibrillation. In the field of cardiac stimulation and monitoring, endocardial leads are placed through a transvenous route to locate, one or more sensing and/or stimulation electrodes along or at the distal end of the lead in a desired location within a heart chamber or interconnecting vasculature. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such a lead is typically formed with a connector which connects to a terminal of the IPG or monitor. The lead body typically comprises one or more insulated conductive wires surrounded by an insulating outer sleeve. Each conductive wire couples a proximal lead connector element with a distal stimulation and/or sensing electrode. An endocardial cardiac lead having a single stimulation and/or sensing electrode at the lead distal end and a single conductive wire is referred to as a unipolar lead. An endocardial cardiac lead having two or more stimulation and/or sensing electrodes at the lead distal end and two or more conductive wires is referred to as a bipolar lead or a multi-polar lead, respectively.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end elect in contact with the endocardium position.

More recently, endocardial pacing and cardioversion/defibrillation leads have been developed that are adapted to be advanced into the coronary sinus and coronary veins branching there from in order to locate the distal electrode(s) adjacent to the left ventricle or the left atrium. The distal end of such coronary sinus leads is advanced through the superior vena cava, the right atrium, the valve of the coronary sinus, the coronary sinus, and may further be advanced into a coronary vein communicating with the coronary sinus, such as the great vein. Typically, coronary sinus leads do not employ any fixation mechanism and instead rely on the close confinement within these vessels to maintain each electrode at a desired site.

Routing an endocardial lead along a desired path to implant the electrode or electrodes in a desired implantation site, either in a chamber of the heart or in the selected cardiac vein or coronary artery, can be difficult. This is particularly true for steering leads through the coronary sinus and into a branching vein on the left myocardium. Anomalies in the vascular anatomy and the number of branch veins associated with the anatomy make locating the desired path challenging.

Several common approaches have been developed to place electrodes within the left side of the heart. According to one approach, a guide catheter is steered into the desired location in the vasculature. A lead is then fed through the inner lumen of the catheter such that the lead electrode(s) are positioned at predetermined locations. The guide catheter may then be withdrawn. This type of approach is described in commonly assigned U.S. Pat. Nos. 6,006,137, 5,246,014, and 5,851,226 incorporated herein by reference. The described systems employ highly flexible, catheters surrounding the lead body.

When using a guide catheter, it may be difficult to locate a desired implant site within the torturous curves of the venous system. This is particularly true if the implant site is located within the coronary sinus or one of the branch veins. To aid in locating the desired implant site, radiopaque dye may be injected into the venous anatomy so that the coronary veins are visible using a fluoroscopic device. This procedure, sometimes referred to as a "venogram", allows the surgeon to determine the appropriate path to be followed when performing the implant.

Venograms may be performed using a catheter having an inflatable balloon located on the distal tip. After the distal tip of the catheter has been located within the appropriate position within the vasculature, such as in the coronary sinus, the balloon is inflated to temporarily occlude the backflow of blood into the vein. The radiopaque dye may then be injected through a catheter lumen located distal to the balloon so that the dye is retained within the vessels long enough to obtain the venogram. The balloon may then be deflated to allow blood flow to resume. The surgeon may then use the map of the cardiac vasculature to steer a pacing or defibrillation electrode to the implant site.

Such a system is described in U.S. Pat. No. 6,122,522 to Tockman which describes a guide catheter having a balloon on a distal tip. After a venogram is taken, the balloon is deflated to allow a guidewire to be passed through a central lumen of the catheter and into the appropriate venous pathway. The guide catheter is then withdrawn from the venous system and a pacing lead is advanced over the guidewire for placement at the implant site.

One disadvantage of the system described in the '522 patent is that once the catheter is withdrawn, another venogram can not readily be obtained. Thus, if the surgeon encounters difficulty in placing the lead, the guidewire and lead must be withdrawn, and the catheter re-inserted within the vasculature. This is time consuming and increases the risk of venous perforation.

What is needed, therefore, is a system and method that allows a venogram to be obtained while a lead is still in place within the vasculature.

SUMMARY OF THE INVENTION

A medical electrical lead having a distal section including an inflatable member such as a inflation member is disclosed. The inflation member is sized such that the inflation diameter engages the walls of a cardiac vein or coronary artery in a manner that fully, or partially, occludes the vessel. In one embodiment, the lead includes a port located distal to the inflation member. This port is in fluid communication with a delivery lumen adapted to deliver radiopaque dye to a vessel when the inflation member is in the inflated state. This allows a fluoroscopic image of a patient's vascular system to be obtained to aid in lead placement.

In one embodiment, the lead carries at least one electrode. For example, if the lead is to be used for uni-polar pacing applications, the lead may carry only a single distal tip electrode. Alternatively, the lead may carry one or more additional electrodes such as anode ring for use in multi-polar sensing and pacing applications. The lead body may further include one or more defibrillation electrodes, and/or may also carry various sensors including pressure and temperature sensors.

According to one aspect of the invention, the lead body also includes a Monolithic Controlled Release Device (MCRD) to elute a therapeutic agent to surrounding tissue in a controlled manner. The device may be located near a distal tip electrode, or elsewhere on the lead body.

The lead may be placed using a guide catheter as is known in the art. The lead may include a lumen adapted to receive a stiffening member such as a stylet to aid in advancing the lead body through the torturous curves of the vascular system.

According to one method of using the inventive system, the inflation member may be inflated after the lead is located at a desired implant site. The inflation member retains the lead at the implant site as the guidewire and/or guide catheter are withdrawn. In one embodiment, the inflation member is formed of a micro-porous or perforated material that allows fluid contained within the inflation member to slowly seep, or "weep", to the exterior of the inflation member. In this manner, an inflation member that is inflated to retain a desired site of implant during the removal of the guidewire and/or guide catheter will deflate a predetermined time thereafter, allowing blood flow to resume in a normal fashion.

In yet another method of using the inventive system, the inflation member is inflated to retain a desired lead position while thresholds are obtained. The inflation member may then be deflated and the lead re-positioned if unacceptable thresholds are measured.

The lead of the current invention may further include a perfusion lumen that is in fluid communication with first and second ports in the side wall of the lead. The first port is located proximal the inflation member, whereas the second port is located distal the inflation member, thereby allowing the flow of blood to partially continue when the inflation member is in the inflated state.

According to yet another embodiment of the invention, the inflation member is formed of a bio-absorbable material so that the inflation member is absorbed by the body a predetermined time after implant.

The distal section of the lead may include a passive or active fixation mechanism. The fixation mechanism may be any of the mechanisms known in the art for maintaining a lead tip within a coronary vein.

Other aspects of the current invention will become apparent to those skilled in the art from the following detailed description, and the accompanying figures.

DETAILED DESCRIPTIONS OF THE DRAWINGS

Figure 1:
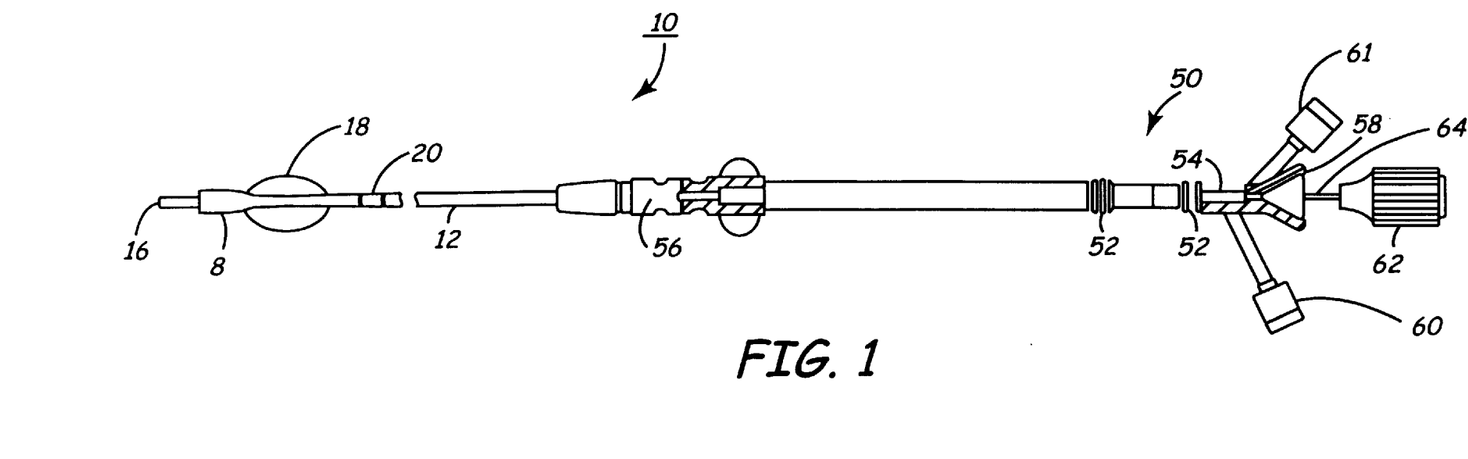
FIG. 1 is a plan view of one embodiment of a lead having an inflatable member such as a balloon mounted on a distal section.

FIG. 1 is a plan view of one embodiment of a lead having an inflatable member such as a balloon mounted on a distal section 8. Lead 10 comprises an elongate lead body 12 and a tip electrode assembly, designated generally by reference numeral 16 in FIG. 1, disposed at the distal section of lead body 12. Distal section of lead body further includes a balloon assembly 18, and a ring electrode 20. Lead body 12 is covered by an insulative sleeve of flexible biocompatible and biostable insulating material, such as polyurethane or silicone rubber. At the proximal end of lead 10, a terminal assembly designated generally as 50 is provided for coupling lead 10 to an implantable pulse generator (not shown). Terminal assembly 50 is provided with sealing rings 52 and a terminal pin 54, all of a type known in the art. An anchoring sleeve 56 may also be provided on lead body 12. As would be familiar to those of ordinary skill in the art, anchoring sleeve 56 slides over lead body 12 and serves as a point for suturing lead body 12 to body tissue at the insertion point of lead 10 in a fashion known in the art. Anchoring sleeve 56 and terminal assembly 50 are preferably fabricated from silicone rubber, although they may also be constructed of any other suitable biocompatible material known in the art.

Lead 10 as shown in FIG. 1 may also include an adapter 58 for coupling to terminal pin 54. Adapter may include a side arm 60 for receiving a syringe to inject fluid into an inflation inner lumen of lead (not shown in FIG. 1) to inflate balloon 18. This is discussed further below. Adapter 58 may further serve as a stylet guide for stylet assembly 62 that is required to impart stiffness to lead 10 during the implantation procedure. Stylet assembly includes a stylet body 64 that is received within an inner lumen (not shown in FIG. 1) of the lead shown in FIG. 1 as a stiffening member to aid in lead placement. Adapter 58 and stylet assembly 60 are discarded after use and before connection of terminal pin 54 to a pacemaker pulse generator.

Figure 2:
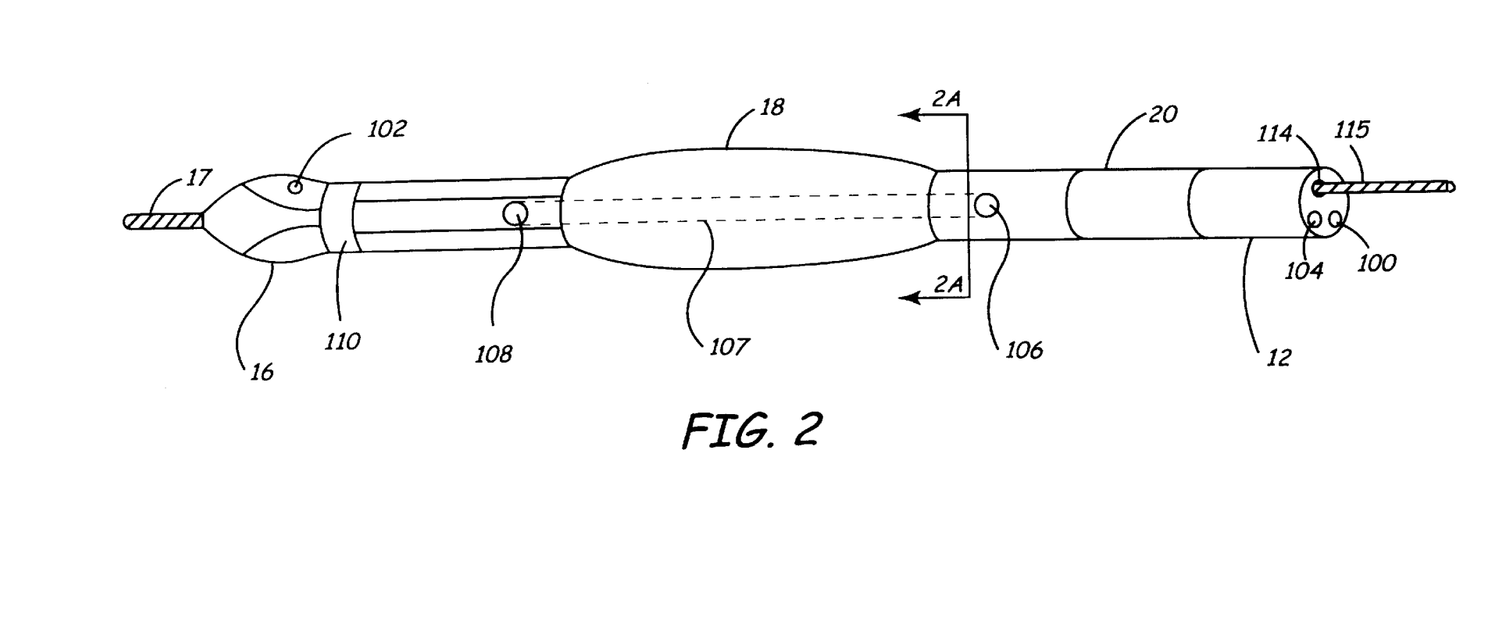
FIG. 2 is an exploded, side cutaway view of distal section of the lead body of the current invention.

FIG. 2 is an exploded, side cutaway view of distal section 8 of lead body 12. Distal section 8 includes tip electrode assembly 16, which could be any of the various types of pacing electrodes known in the art such as a porous platinized electrode assembly. Alternatively, it could be a steroid-eluting porous pacing electrode, as described in U.S. Pat. No. 4,506,680 to Stokes, and related U.S. Pat. Nos. 4,577, 642; 4,606,118; and 4,711,251, all commonly assigned to the assignee of the present invention and incorporated by reference herein in their respective entireties. The electrode disclosed in the Stokes '680 patent is constructed of porous, sintered platinum, titanium, or the like, for example.

Proximal to the tip electrode assembly 16 is a balloon assembly 18. The balloon may be formed of compliant or non-compliant polymer materials. Example of materials that are suitable for balloon construction include polyethelene, nylon, PET, and laytex. In one embodiment, the balloon is formed of polyurethane (Pellathane) having a stiffness of approximately 80A Shore which is available from World Medical of Miami, Fla. In yet another embodiment, the balloon may be constructed of a material that is permeable, or that has micro-pores to allow the fluid from within the balloon to slowly seep to the balloon exterior. A "weeping" balloon of this type is described in U.S. Pat. No. 5,087,244 to Wolinsky et al. which is incorporated by reference in its entirety. In one embodiment, the balloon has an inflated diameter of between approximately 1.5 to 4 mm, and a length of between approximately 10 to 40 mm. The balloon may be attached to the lead body using a thermal or adhesive, as is known in the art.

Balloon 18 is fluidly coupled to an inflation lumen 100. A syringe inserted in side arm 60 (FIG. 1) may inject fluid into inflation lumen 100 to inflate balloon 18 to a size that partially, or fully, occludes a vessel in which lead 10 is placed. A port 102 located in tip electrode assembly 16 distal to the balloon is provided to deliver fluoro-visible media to a vessel when the balloon is inflated. This allows a venogram to be taken while the lead remains in position at the desired implant side. Fluid, including the fluoro-visible media, is delivered to port 102 via fluid delivery lumen 104 that extends to side arm 61, which is adapted to receive a syringe. Port 102 may further be utilizes to deliver any other type of fluid, including therapeutic drugs.

In one embodiment, lead 10 includes a perfvsion lumen 107 (shown dashed in FIG. 2). Perfusion lumen 107 is fluidly coupled to a proximal port 106 and a distal port 108 in lead body 12. When balloon 18 is inflated within a vessel, blood flow continues through perfusion lumen so that a complete blockage of the vessel does not occur. This allows the balloon to remain inflated for an extended period of time without causing necrosis of tissue within the vessel, which may be desirable if the balloon is to be used as a fixation device in a manner to be discussed below.

Lead 10 may further include a Monolithic Controlled Release Device (MCRD) 110 such as disclosed in commonly-assigned U.S. Pat. No. 4,506,680 incorporated herein by reference. An MCRD is designed to elute a therapeutic agent to surrounding tissue in a controlled manner. Such a device may be fabricated of a polymer such as a polyurethane, polyurea or polyurethane polyurea. The MCRD does not expand significantly when exposed to body fluid and therefore may be mounted, exposed to, or located on the exterior surface of, a pacing lead. The release device may be cast or molded to a desired shape, and may be located adjacent to, or on, the electrode surface. The MCRD may be fabricated as a polymer composite which is readily adhesively bonded to other components of the lead. For example, a polyurethane MCRD is readily adhered to a pacing lead having a polyurethane insulative sheath, or molded polyurethane components adjacent to the electrode. The MCRD may also be mechanically attached to the pacing lead.

In some embodiments, the release device is configured as an annular member encircling the distal tip electrode 16 of lead 10. This allows the MCRD to elute a steroid or other agent in the vicinity of the electrode, without requiring delivery of a agent through the electrode. Alternatively, the MCRD may be located within a lumen or recess at the distal tip of the lead. Steroid may then elute from the bulk of the MCRD into body fluid within the lumen, and then contact the tissue adjacent to the tip of the lead. By limiting the surface available for elution primarily to the interior of the lead, dissipation of the steroid into the bloodstream is reduced. Because the MCRD is generally dimensionally stable, it will not expand to the degree that it interferes with the operation of a fixation device associated with the distal tip electrode assembly.

The lead of FIG. 2 is further shown to include a ring electrode 20. Distal tip electrode assembly 16 is used in conjunction with ring electrode 20 for bipolar pacing and sensing applications. If only monopolar applications are to be provided, ring electrode 20 is not needed.

Figures 3, 4:
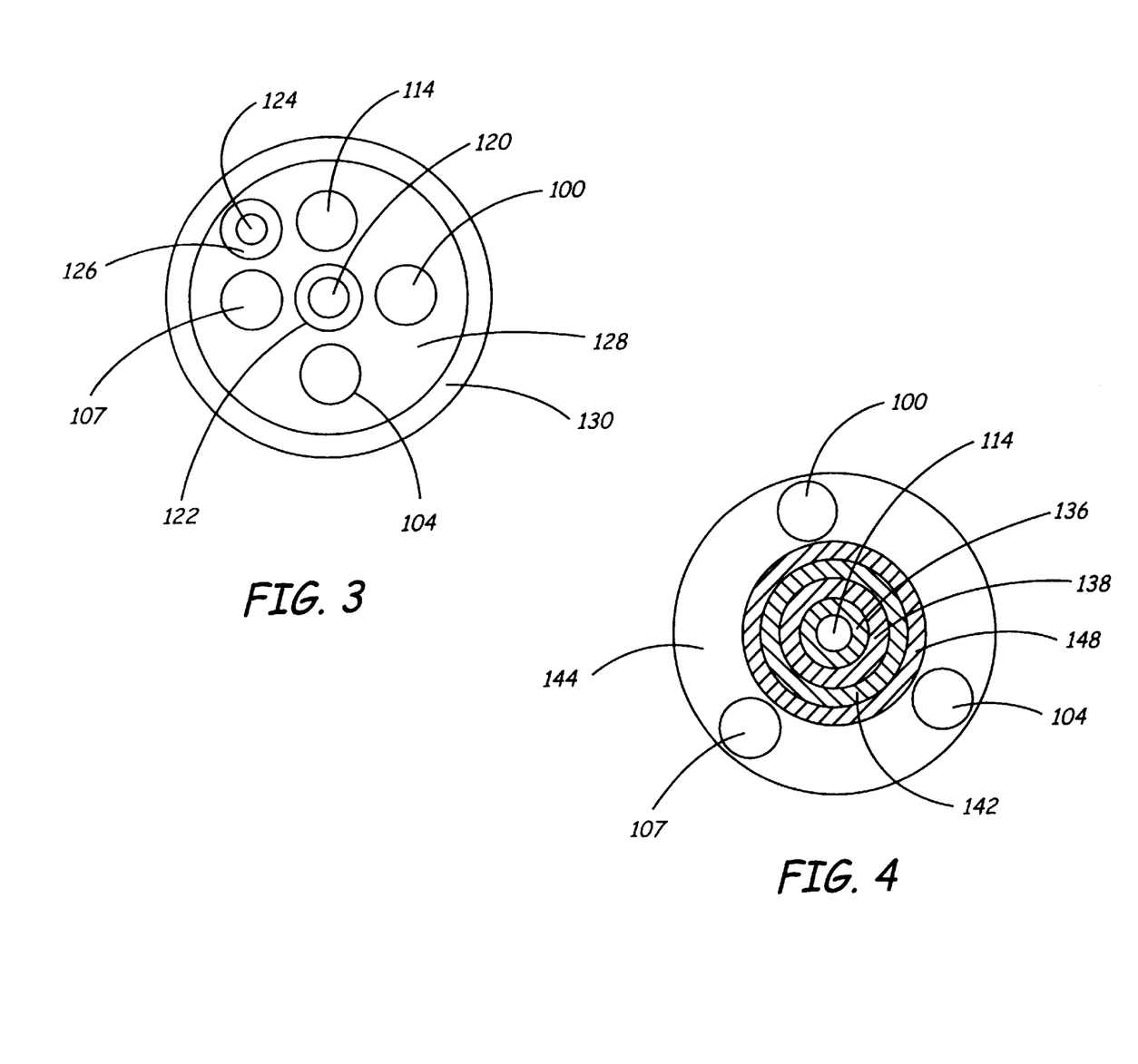
FIG. 3 is a cross-sectional view of the lead of the current invention at line 2A—2A.
FIG. 4 is a cross-section view of another embodiment of the lead of the current invention at line 2A—2A.

FIG. 3 is a cross-sectional view of lead 10 at line 2A—2A. As discussed above, in this embodiment lead 10 includes inflation lumen 100, fluid delivery lumen 104, and perfusion lumen 107. It may also include stylet lumen 114 to be discussed below. Lead 10 is further shown to include a first conductor 120 in central lumen 122, and second conductor 124 included in lumen 126. Each of the conductors 120 and 124 couples to a respective one of the distal tip electrode 16 and the ring electrode 20. This type of multiconductor, multi-lumen lead design is described in U.S. Pat. No. 5,584,873 issued to Shoberg, et al. incorporated herein by reference.

The conductors may take the form of either stranded or cabled conductors, as described in the '873 patent. A stranded design adaptable for use with the current invention corresponds to that disclosed in U.S. Pat. No. 5,246,014 issued to Williams et al, also incorporated herein by reference in its entirety. Other conductor types may of course also be employed, including twenty-strand cables, as described in U.S. Pat. No. 5,845,396 issued to Altman et al, also incorporated herein by reference in its entirety. In still other embodiments, the individual conductors may simply take the form of a single filar wire conductor, wound around the core member of the lead body. The lead may alternatively including multiple conductors separated by insulative strands or tubes and wound around a generally cylindrical or tubular, insulative core member, as described in commonly-assigned application entitled "Electrically-Isolated Multiple Conductor Lead Body", Ser. No. 09/598,983, filed Jun. 21, 2000, and incorporated herein by reference.

The various lumens shown in FIG. 3 are surrounded by a biocompatible insulative polymer 128 such as polyurethane, silicone rubber, or the like. Lead 10 may further include a protective jacket formed of urethane, silicone, or and other biocompatible material. This jacket offers an abrasion-proof layer that increases lead stiffness to afford better pushability and torque control.

FIG. 4 is a cross-section view of another embodiment of lead 10 at line 2A—2A. In this embodiment, the multi-conductor lead is of a coaxial design, wherein multiple coiled conductors are mounted around one another, separated by tubular insulative sheaths, as described in U.S. Pat. No. 4,355,646 issued to Kallok, incorporated herein by reference. A central lumen may be provided as stylet lumen 114, for example. Central lumen is surrounded by a layer 136 of insulative sheath. Coiled conductors 138 and 140 are separated by a second insulative sheath 142. Insulative material 144 surrounds insulative sheath 142, and includes the remaining lumens, including the inflation lumen 100, fluid delivery lumen 104, and perfusion lumen 107.

FIGS. 2 through 4 are intended to be purely exemplary of the type of lead in which the invention may be usefully practiced. Other electrode or connector types may, of course, be substituted. Additional electrodes may be added, or electrodes may be deleted. In addition, it should also be understood that the lead body of the present invention is useful in the context of leads carrying one or more physiologic sensors, for example, carrying an oxygen sensor as disclosed in U.S. Pat. No. 4,903,701 issued to Moore et al, a pressure sensor as disclosed in U.S. Pat. No. 4,967,755 issued to Pondorf or a temperature sensor as disclosed in U.S. Pat. No. 5,081,988, issued to Cook, et al., all of which patents are incorporated herein by reference in their entireties, or carrying any other physiologic sensor.

As the number of electrodes and/or sensors increases, the required number of mutually insulated conductors within the lead body correspondingly increases. Additional embodiments of the lead may include embedding multiple conductors within the wall of an insulative lead body, as disclosed in U.S. Pat. No. 5,968,087 issued to Hess, et al., U.S. Pat. No. 5,016,646 issued to Gotthardt, et al. and U.S. Pat. No. 5,845,396 issued to Altman et al. An additional alternative approach is disclosed in U.S. Pat. No. 5,935,159 issued to Cross et al, in which individual conductors are separated from one another by means of a central strut having laterally extending projections, serving to space and insulate adjacent conductors from one another, within a tubular outer sheath.

Alternatively, the number of electrodes and conductors may be decreased. In a uni-polar embodiment of the inventive lead having only distal tip electrode 16 and omitting ring electrode 20, only a single conductor is carried by lead body 12.

Figure 5:
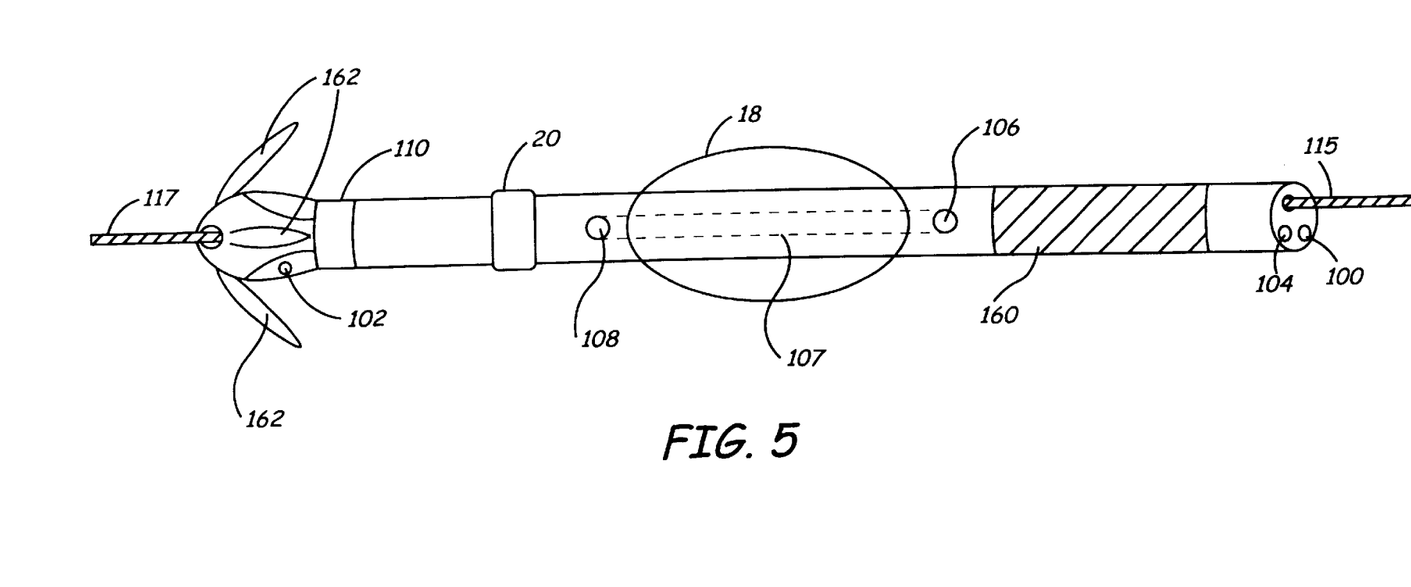
FIG. 5 is a plan view of another embodiment of the inventive lead with the balloon positioned proximal to the ring electrode, and further including a defibrillation electrode.

FIG. 5 is a plan view of another embodiment of lead 10 with balloon 18 positioned proximal to ring electrode 20, and further including a defibrillation electrode 160. Defibrillation electrode 160 is a coiled electrode of conventional design. One or more such electrodes may be spaced along lead body 12 to facilitate their location, for example, in the superior vena cava and right ventricle of the heart, respectively. In some embodiments, one or more defibrillation electrodes may be embedded in lead body 12 to provide an isodiametric lead configuration, as disclosed in U.S. Pat. No. 4,161,952 issued to Kinney et al, or U.S. Pat. No. 5,957,970 issued to Shoberg, et al., both also incorporated herein by reference in its entirety.

FIG. 5 further shows fixation tines 162 included in distal tip electrode assembly 16. Such pliant tines or barbs are known in the art as a passive fixation mechanism for securing the electrode at the desired location of implant by engaging the trabeculae within the heart chamber. As an alternative, an "active" fixation mechanism may be used, including corkscrews, hooks, piercing barbs or other anchoring structures arranged at or near the distal tip for penetration of cardiac tissue upon proper positioning of the electrode. Yet other mechanisms are available for securing leads placed within cardiac veins such as the coronary sinus. Fixation devices of this nature are disclosed in U.S. Pat. Nos. 5,964,795, 6,006,122, and 5,387,233 which are incorporated herein by reference.

Returning now to FIG. 2, this Figure further shows a guidewire 115 inserted within stylet lumen 114 of lead 10. As is known in the art, a distal tip 115 of guidewire 115 may be used to locate a predetermined implant site. The lead may be then advanced over the guidewire via stylet lumen 114. The body of the guidewire may be of any conventional design such as that described in commonly-assigned U.S. Pat. No. 4,815,478 to Buchbinder et al., incorporated herein by reference in its entirety. Suitable alternative guidewire systems are described in U.S. Pat. Nos. 5,095,915, 4,545,390, or 5,746,710, all incorporated by reference herein in their entirety.

Alternatively, it may be desirable to use a stylet such as stylet assembly 62 (FIG. 1) to deliver lead 10. According to this method of delivery, a guide catheter is advanced to the implant site. A lead pre-loaded with a stylet may then be advanced within the guide catheter to the implant location. The stylet and catheter are retracted, leaving the lead in place.

One example of a stylet which may be used for delivery of lead 10 is disclosed in commonly-assigned U.S. Pat. No. 4,350,169 entitled "Flexible Tip Stiffening Stylet for Use With Body Implantable Lead", and which is incorporated herein by reference. Alternatively, a stylet having a pull-wire to deflect the distal tip may be utilized, such as that disclosed in U.S. Pat. No. 5,873,842 incorporated herein by reference. In another embodiment, a stylet with a shapeable tip may be used to steer the lead to the desired location of implant. For example, commonly assigned U.S. Pat. No. 4,381,013 to Dutcher is directed to the use of a two-piece stylet having an inner solid portion for enabling a shape to be imparted to the lead to facilitate introduction into a predetermined implant site. The stylet further includes a tubular portion which enables the transmission of torque applied by the implant physician at the proximal end to be transmitted to a fixation means located on the distal end of the lead.

Figure 6:
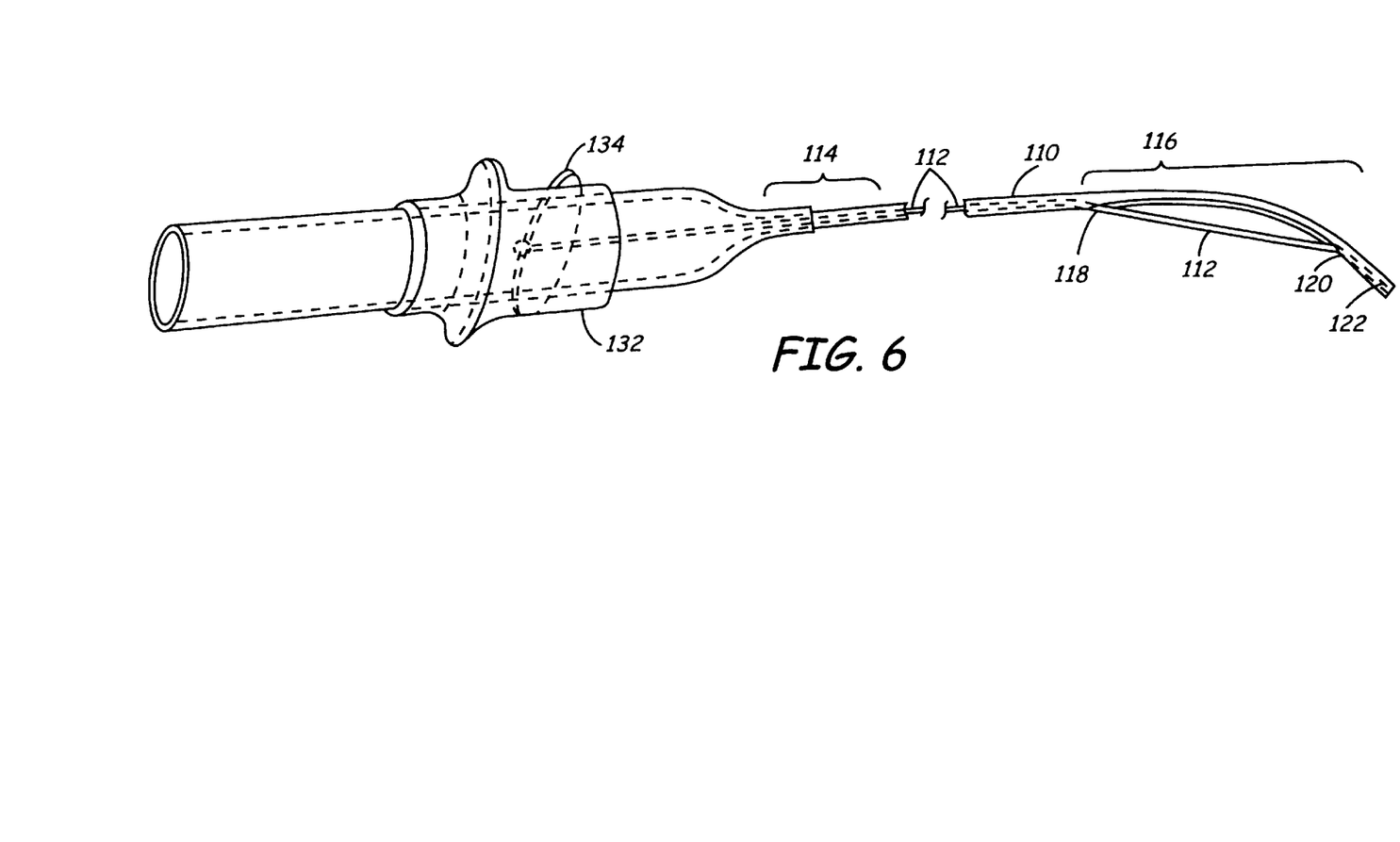
FIG. 6 is a perspective view of one embodiment of a steerable stylet that may be used with the current invention.

FIG. 6 is a perspective view of one embodiment of a steerable stylet that may be used with the current invention. The steerable stylet, which is disclosed in the '842 patent referenced above, comprises the elongated tubular member 110 and pull wire 112 having a proximal section 114 and a distal section 116 with an elongated intermediate section extending there between (not specifically illustrated). The distal section 116 possesses first and second apertures 118 and 120 separated by a predetermined distance. A radius of curvature is imparted as the pull wire 112 is retracted proximally. The pull wire 12 mechanically cooperates with the distal tip 122 of the tubular member 110 to accomplish tip deflection. The manipulative handle of the stylet assembly includes slidable member 132, and lever 134 attached to the proximal portion 114 of the pull wire 112. In use, curvature is imparted to distal tip 122 by the thumb engageable, slideable member 132 acting on the lever 134 and pull wire 112. Of course, FIG. 6 is merely one example of a stylet that is adaptable for use with the current invention, and one skilled in the art will appreciate that many other types of stylet designs known in the art may be adapted for use with the lead of the current invention.

As noted above, placement of the lead and stylet assembly of the current invention may be accomplished using a guide catheter or introducer sheath as is known in the art. For example, the introducer may be of a design similar to the SHERPA® guide catheters sold by Medtronic, Inc. Other exemplary structures of guide catheters are disclosed in U.S. Pat. No. 5,755,704 issued to Lunn, U.S. Pat. No. 5,545,149, issued to Brin, et al. and U.S. Pat. No. 5,811,043 issued to Horrigan, et al., all incorporated herein by reference in its entirety. The guide catheter may be steerable using one or more pull wires included within the walls of the catheter.

During lead placement, the guide catheter may be navigated to a desired implant site using a steering mechanism provided by the catheter itself, or using a guidewire inserted within an inner lumen of the guide catheter. If a guide wire is used to steer the assembly to the implant site, the guide wire is removed from the catheter lumen so that the lead assembly may be inserted into this lumen. Lead 10, including stylet assembly 62 that is inserted into stylet lumen 114 of lead 10, is then advanced through the inner lumen of the guide catheter.

If additional information is require regarding the curvature of the vasculature, distal end of lead 10 may be extended past the distal end of introducer, balloon 18 may be inflated in the manner discussed above, and a venogram may be taken.

After distal tip electrode 16 is placed in the proper location, stylet 64 may be withdrawn from lumen 114. Additionally, the guide catheter may also be withdrawn. To aid in maintaining the electrode position with the stylet and guide catheter are removed, balloon 18 may be inflated so that the inflated diameter of the balloon contacts the walls of the patient's vasculature. In this embodiment, a weeping balloon of the type disclosed above is preferred. The weeping balloon may be filled with a liquid such as saline, which will gradually seep into the patient's body through the micro-porous material of the balloon. This will allow the balloon to gradually deflate after the guidewire and guide catheter have been successfully removed from the patient's vasculature.

In one embodiment, balloon 18 is formed of a bio-absorbable material such as any of the commonly known bio-absorbable polymers. The balloon of this embodiment can be left in the inflated state after the implant procedure is completed. This will aid in fixing the lead at the desired implant site for a predetermined period of time until tissue in-growth begins. The balloon material will eventually be absorbed by the patient's body. It may be noted that perfusion lumen 107 allows for partial blood flow after initial implant so that tissue necrosis will not result during the time the balloon is inflated.

According to another method of using the present invention, the balloon may be inflated to temporarily retain the lead in a desired position while thresholds are measured, for example. If necessary, the balloon may be deflated so that the lead 10 may be re-positioned, and the process repeated.

Variations and modifications to the present invention may be possible given the above disclosure. However, all such variations and modifications are intended to be within the scope of the invention claimed by this letters patent.

In conjunction with the above disclosure, we claim:

1. A medical electrical lead for use in a body, comprising:
    an elongated lead body having a proximal end and a distal end; and
    an inflatable member coupled to the distal end of the lead adapted to selectively engage a cardiac vein or coronary artery, wherein the inflatable member is formed of a bio-absorbable material.

2. The lead of claim 1, and further including a first perfusion port proximal the inflatable member, a second perfusion port distal the inflatable member, and a perfusion lumen to couple to the first and second perfusion ports.

3. The lead of claim 1, wherein the lead includes a delivery lumen adapted to deliver a predetermined substance to the body.

4. The lead of claim 1, wherein the elongated lead body further includes a Monolithic Controlled Release Device (MCRD).

5. The lead of claim 1, and including at least one electrode carried on the elongated lead body.

6. The lead of claim 5, wherein the at least one electrode includes a distal tip electrode and a ring electrode.

7. The lead of claim 5, wherein the at least one electrode includes a defibrillation electrode.

8. The lead of claim 1, wherein the elongated lead body includes a lumen for receiving a stiffening member.

9. A method for placing a lead within a body, including the methods of:
    a.) placing a lead at a predetermined implant site within the body;
    b.) inflating a inflation member carried on the lead to at least partially occlude a vessel of the body, and maintaining the inflation member in the inflated position for a predetermined period of time until tissue in-growth begins to occur;
    c.) releasing fluoro-visible medium from a port located distal of the inflation member on the lead; and
    d.) using the fluoro-visible medium to obtain data indicative of the body structure, wherein the method of maintaining the inflation member in the inflated position for a predetermined period of time is accomplished by allowing liquid inside the inflation member to diffuse into the body at a predetermined rate.

10. The method of claim 9, and further including the method of deflating the inflation member and re-positioning the lead at a second predetermined implant site within the body.

11. The method of claim 9, wherein step a.) includes the step of utilizing a guide catheter to place the lead at the predetermined implant site.

12. The method of claim 11, and further including the method of maintaining the inflation member in the inflated position to retain the lead at the predetermined implant site while the guide catheter is withdrawn from the body.

13. The method of claim 12, wherein step a.) further includes the step of utilizing a guide wire inserted in a lumen of the lead to place the lead at the predetermined implant site.

14. The method of claim 13, and further including the method of maintaining the inflation member in the inflated position to retain the lead at the predetermined implant site while the guide wire is withdrawn from the body.

15. The method of claim 9, wherein method b.) further includes the method of providing an perfusion lumen to allow fluid within the body to flow around the inflated inflation member.

16. A method for placing a lead within a body, including the methods of:
    a.) placing a lead at a predetermined implant site within the body;
    b.) inflating a inflation member carried on the lead to at least partially occlude a vessel of the body, and maintaining the inflation member in the inflated position for a predetermined period of time until tissue in-growth begins to occur;
    c.) releasing fluoro-visible medium from a port located distal of the inflation member on the lead; and
    d.) using the fluoro-visible medium to obtain data indicative of the body structure, wherein the method of maintaining the inflation member in the inflated position for a predetermined period of time is accomplished by providing an inflation member formed of bio-absorbable material that is absorbed by the body at a predetermined rate.

* * * * *